(12) United States Patent
Revel et al.

(10) Patent No.: US 7,201,896 B1
(45) Date of Patent: Apr. 10, 2007

(54) IL6RIL6 CHIMERA FOR THE TREATMENT OF NEURODEGENERATIVE DISEASES

(75) Inventors: Michel Revel, Rehovot (IL); Judith Chebath, Rehovot (IL); Marina Pizzi, Brescia (IT); PierFranco Spano, Milan (IT); Ursula Boschert, Troinex (CH)

(73) Assignees: Yeda Research and Development Company Ltd., Rehovot (IL); Applied Research Systems ARS Holding N.V., Curacao, Netherlands Antilles (NL)

( * ) Notice: Subject to any disclaimer, the term of this patent is extended or adjusted under 35 U.S.C. 154(b) by 343 days.

(21) Appl. No.: 09/980,823

(22) PCT Filed: Jun. 21, 2000

(86) PCT No.: PCT/IL00/00363

§ 371 (c)(1),
(2), (4) Date: Aug. 28, 2002

(87) PCT Pub. No.: WO00/78331

PCT Pub. Date: Dec. 28, 2000

(30) Foreign Application Priority Data

Jun. 21, 1999 (IL) .................................... 130586

(51) Int. Cl.
*A61K 38/20* (2006.01)
*A61K 45/00* (2006.01)
*C07K 14/54* (2006.01)

(52) U.S. Cl. ...................... 424/85.2; 424/85.1; 514/12; 530/351

(58) Field of Classification Search ................. 530/351; 424/85.2; 514/12, 903
See application file for complete search history.

(56) References Cited

FOREIGN PATENT DOCUMENTS

| JP | 1999/0048413 A | 2/1999 |
| WO | WO 99/02552 | 1/1999 |

OTHER PUBLICATIONS

Barinaga, M. Science, vol. 264, pp. 772-773, May 1994.*
XP-002156155—Haggiag et al., "Induction of myelin gene expression in cell cultures by an IL6 receptor IL6 chimera", *Neuroscience Letters*, 54:S19 (1999).
XP-002156153—Haggiag et al., "Induction of myelin gene expression in Schwann cell cultures by an interleukin-6 receptor-interleukin-6 chimera", *FEBS Letters*, 457:200-204 (1999).
XP-000971298—Ringheim et al., "Enhancement of beta-amyloid precursor protein transcription and expression by the soluble interleukin-6 receptor/interleukin-6 complex", *Molecular Brain Research*, 55:35-44 (1998).

* cited by examiner

*Primary Examiner*—Eileen O'hara
*Assistant Examiner*—Fozia Hamud
(74) *Attorney, Agent, or Firm*—Browdy and Neimark, PLLC

(57) ABSTRACT

The invention relates to the use of IL6RIL6 chimera in the treatment and prevention of neurological diseases and disorders.

4 Claims, 6 Drawing Sheets

A

B

IL6RIL6 CHIMERA FOR THE TREATMENT OF NEURODEGENERATIVE DISEASES

REFERENCE TO RELATED APPLICATIONS

The present application is the national stage under 35 U.S.C. 371 of international application PCT/IL00/00363, filed Jun. 21, 2000 which designated the United States, and which international application was published under PCT Article 21(2) in the English language.

FIELD OF THE INVENTION

The present invention is generally in the field of neurological diseases and disorders. In particular it relates to neurodegenerative diseases, neuroprotection, nerve myelination and generation of cells which produce the myelin sheath. More particularly, the present invention provides for the use of IL6RIL6 chimeras for the manufacture of a medicament for treatment of neurological diseases or disorders, especially for neuroprotection and for the treatment of demyelinating diseases and the enhancement of nerve regeneration.

BACKGROUND OF THE INVENTION

Nerve myelination is an essential process in the formation and function of the central nervous system (CNS) and peripheral nervous system (PNS) compartments. The myelin sheath around axons is necessary for the proper conduction of electric impulses along nerves. Loss of myelin occurs in a number of diseases, among which are Multiple Sclerosis (MS) affecting the CNS, Guillain-Barre Syndrome, CIDP and others (see Abramsky and Ovadia, 1997; Trojaborg, 1998, Hartung et al, 1998). While of various etiologies, such as infectious pathogens or auto-immune attacks, demyelinating diseases all cause loss of neurological functions and may lead to paralysis and death. While present therapeutical agents reduce inflammatory attacks in MS and retards disease progression, there is a need to develop therapies that could lead to remyelination and recovery of neurological functions (Abramsky and Ovadia, 1997, Pohlau et al, 1998).

The synthesis of myelin is a function of specialized glial cells: the oligodendrocytes in the CNS and the myelinating Schwann cells in the PNS. These two cell types in their fully differentiated state may be called myelinating cells. Myelin is a lipid membrane structure containing a number of different proteins. Myelin basic proteins (MBP) represent the major components (30%) of CNS and also of PNS myelin proteins. Expression of the MBP and other genes encoding the various myelin proteins (e.g. P0, PMP-22, MAG in PNS, PLP, MOG in CNS), is turned on during the terminal differentiation of oligodendrocytes and myelinating Schwann cells. The origin of these cells is in the embryonal neural crest (Fraser, 1991) from which they migrate, and undergo a differentiation that proceeds in a number of steps. Schwann cell (SC) development appears to involve three main steps: 1) the generation of precursors (pSC) from migrating cells; 2) the proliferation and transition to embryonic SC (eSC) expressing the S100 protein; 3) the postnatal terminal differentiation of part of the eSC population into myelinating SC that express MBP and other myelin proteins (Kioussi and Gruss, 1996). The cells migrating from the neural crest give rise not only to pSC but also to sensory and sympathic neurons, to smooth muscle cells and to cells which reach the skin and hair follicles and become pigmented melanocytes. The fate of the neural crest cells is affected by various inducing factors: differentiation to glial cells, to neurons and to muscles is promoted by Neuregulins such as glial growth factor (GGF), by BMP2/4 and by TGF-β respectively (Anderson, 1997). The differentiation to melanocytes may be promoted by growth factors such as bFGF or PDGF or SDF (Stocker et al., 1991; Anderson, 1997).

The ultimate differentiation of Schwann and oligodendrocyte progenitors into actively myelinating cells and myelination itself seems to depend on signals generated by the interaction between neuronal axons and the glial cells (Lemke and Chao, 1988; Trapp et al, 1988). When axon-Schwann cell contact is interrupted, as after nerve damage, the cells reverse to a non-myelinating state and expression of myelin protein genes is lost (Jessen and Mirsky, 1991). To be able to stimulate myelination or remyelination, after neural diseases or trauma, it would be extremely important to identify factors that are able to induce the synthesis of myelin.

Injury to CNS induced by acute insults including trauma, hypoxia and ischemia can affect both neurons and white matter. Although most attention has been paid to processes leading to neuronal death, increasing evidence suggests that damage to oligodendrocytes, which myelinate axons, is also a specific component of CNS injury. Thus oligodendrocyte pathology was demonstrated at very early phase after brain ischemia (3 hours) in rats, suggesting that these cells are even more vulnerable to excitotoxic events than neuronal cells (Pantoni et al. 1996). One potential candidate mediating cell death is the marked elevation of glutamate concentration that accompanies many acute CNS injuries (Lipton et al. 1994). Indeed, beside neurons even oligodendrocytes were found to express functional glutamate receptors belonging to the AMPA/kainate subtype. Moreover oligodendrocytes display high vulnerability to glutamate application (McDonald et al. 1998).

Neuregulins such as GGF, which act on embryonic Schwann cell precursors, are also survival, growth and maturation factors for postnatal oligodendrocytes and Schwann cells in damaged nerves, and GGF is one of the mitogenic factors provided by axonal contact (Topliko et al, 1996). Recombinant hGGF2 could enhance remyelination upon prolonged administration in a murine model for Multiple Sclerosis (Cannella et al, 1998) or in crushed peripheral nerve (Chen et al, 1998). Another cytokine that is induced in Schwann cells by axonal contact is the Ciliary neurotrophic factor CNTF (Lee et al, 1995). CNTF, as well as leukemia inhibitory factor (LIF), was shown to promote survival of oligodendrocytes from optic nerve cultured in vitro with bFGF or PDGF, and to increase the number of MBP expressing oligodendrocytes in these cultures (Mayer et al, 1994). However, when added to glial precursor cells, CNTF and LIF appear rather to favor astrocyte differentiation and induce expression of the astrocyte GFAP marker, while on oligodendrocytes it would have mainly a survival action with little effect on the level of MBP gene expression (Kahn and De Vellis, 1994, Bonni et al, 1997). Nevertheless, combinations of CNTF with brain-derived neurotrophic factor BNDF improve recovery of an injured peripheral sciatic nerve (Ho et al, 1998).

CNTF and LIF are cytokines acting through a common receptor system which comprises the LIF receptor (LIFR) and the gp130 chain, the latter being also part of the Interleukin-6 (IL-6) receptor complex (Ip et al, 1992). CNTF and LIF are, therefore, part of the IL-6 family of cytokines. In the case of CNTF and LIF, signal transduction operates through dimerization of LIFR with gp130, whereas in the case of IL-6 the signal is generated by the dimerization of two gp130 chains (Murakami et al, 1993). In order to bind gp130, IL-6 makes a complex with an IL-6 Receptor chain, which exists on certain cells as a gp80 transmembrane protein but whose soluble form can also function as an IL-6 agonist when provided from outside the cell (Taga et al, 1989, Novick et al, 1992). By fusing the entire coding regions of the cDNAs encoding the soluble IL-6 receptor (sIL-6R) and IL-6, a recombinant IL6RIL6 chimera can be produced in CHO cells (Chebath et al, 1997, WO99/02552). This IL6RIL6 chimera has enhanced IL-6-type biological activities and it binds with a much higher efficiency to the gp130 chain in vitro than does the mixture of IL-6 with sIL-6R (Kollet et al, 1999).

A review of the effects of IL-6 on cells of the central and peripheral nervous system indicates that the cytokine may have protective effects on neuronal cells as well as participate in inflammatory neuro-degenerative processes (Gadient and Otten, 1997, Mendel et al, 1998). On glial cells, CNTF and LIF were much more active than IL-6 to stimulate astrocyte differentiation and there was no effect on myelin protein producing cells (Kahn and De Vellis. 1994). IL-6 was found to prevent glutamate-induced cell death in hippocampal (Yamada et al. 1994) as well as in striatal (Toulmond et al. 1992) neurons. The IL-6 mechanism of neuroprotection against toxicity elicited by NMDA, the selective agonist for NMDA subtype of glutamate receptors, is still unknown. In fact IL-6 was found to enhance the NMDA-mediated intracellular calcium elevation. In transgenic mice expressing higher levels of both IL-6 and soluble IL-6R (sIL6-R), an accelerated nerve regeneration was observed following injury of the hypoglossal nerve as shown by retrograde labeling of the hypoglossal nuclei in the brain (Hirota et al, 1996). In that work, the addition of IL-6 and sIL-6R to cultures of dorsal root ganglia (DRG) cells showed increased neurite extension in neurons, but no effect on myelinating cells was reported.

In the light of the data presented above, CNTF, LIF or a mixture of IL-6 and sIL-6R have not been shown to induce the terminal differentiation of glial cells into myelinating cells. However, as outlined above, stimulation of myelinating cells differentiation would be of great benefit for patients suffering from demyelinating or neurodegenerative diseases.

Citation of any document herein is not intended as an admission that such document is pertinent prior art, or considered material to the patentability of any claim of the present application. Any statement as to content or a date of any document is based on the information available to applicants at the time of filing and does not constitute an admission as to the correctness of such statement.

SUMMARY OF THE INVENTION

It is the object of the present invention to provide means for the treatment and/or prevention of neurological diseases or disorders. In particular, it is an object of the present invention to provide a means to stimulate or enhance the differentiation of progenitors or differentiated glial cells into myelinating cells. The basis of the invention is in the use of the recombinant IL6RIL6 chimera protein, which has a markedly higher affinity for gp130 than does the mixture of IL-6 and sIL-6R.

It is further an object of the present invention to provide a means to stimulate or enhance the myelination or remyelination of injured fibers as illustrated by the induced remyelination of axons following sciatic nerve axotomy in vivo further to the myelinating effects of the IL-6 chimera on the induction of myelin genes in vitro.

It is also an object of the present invention to use the IL6RIL6 chimera for increasing the number of Schwann cells developing in dorsal root ganglia (DRG) cultures. Furthermore, it is an object of the present invention to use the IL6RIL6 for induction of the differentiation of these cells to the point where they wrap around axons and produce myelin basic protein as illustrated in cocultures of Schwann cell lines with primary DRG.

It is another object of the present invention to use the IL6RIL6 chimera for induction the transcription of the myelin basic protein (MBP) genes in a system of transdifferentiation in which cells with melanocytic phenotype are converted into a Schwann, myelinating phenotype, as illustrated by the effect of IL6RIL6 on a murine melanoma.

It is another object of the present invention to use the IL6RIL6 chimera as a neuroprotective agent and for prevention of neuronal cell death in the hippocampus, a region involved in memory encoding and one that exhibits early degeneration in Alzheimer's disease and ischemia.

It is another object of the present invention to use the IL6RIL6 chimera as a protective agent against the neurotoxicity process triggered by excitatory amino acids as illustrated by the protection from glutamate-induced neurotoxicity provided by the IL-6 chimera in primary cultures of new born rat cerebella neurons.

A molecular mechanism is proposed by which the IL6RIL6 induces and represses specific transcription factors that bring about the induction of the MBP gene differentiation into myelinating phenotype.

Thus, the present invention provides the use of IL6RIL6 chimera for the manufacture of a medicament for the treatment and/or prevention of neurological diseases and disorders. In particular, the present invention provides the use of IL6RIL6 chimera for the manufacture of a medicament for treating traumatic nerve degeneration, demyelinating diseases of the CNS or PNS and/or neurodegenerative diseases.

More particularly, the invention provides for the use of IL6RIL6 chimeras in the treatment of multiple sclerosis (MS), Alzheimer's disease, Parkinson's disease or ALS.

The invention also provides pharmaceutical compositions comprising IL6RIL6 chimera, optionally together with one or more pharmaceutically acceptable excipients, for the treatment and/or prevention of neurological disease and disorders. In particular the pharmaceutical composition is for treating traumatic nerve degeneration, demyelinating diseases of the CNS or PNS and/or neurodegenerative diseases.

A preferred use for the pharmaceutical compositions of the present invention is the treatment of MS, Alzheimer's disease, Parkinson's disease or ALS.

DETAILED DESCRIPTION OF THE INVENTION

Figure 1:
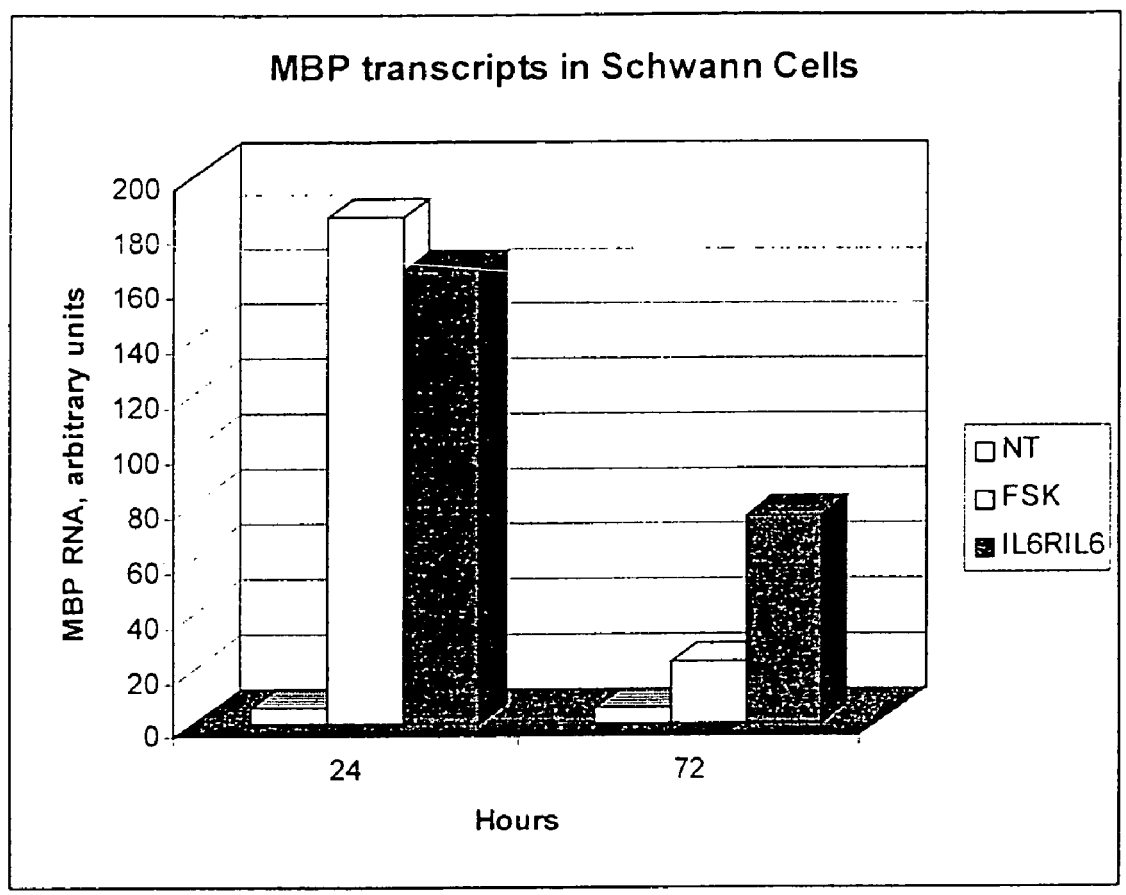
FIG. 1 shows the increase in MBP RNA in cultures of Schwann cells treated by IL6RIL6 chimera or by forskolin (FSK) or left untreated (NT).

In accordance with the invention it has been found that addition of IL6IL6R recombinant protein to cultures of dorsal root ganglia cells or of melanoma cells stimulates the differentiation of those cells into myelinating cells. It was also found that the addition of the IL6IL6R recombinant protein to cocultures of neurons and Schwann cells induces the latter to form a regular sheath around the axons. The invention therefore relates to the use of the IL6RIL6 chimera for the manufacture of a medicament to generate myelinating cells or to stimulate, enhance or accelerate the generation of myelinating cells.

The IL-6 chimera further induces in vivo remyelination of transected fibers following sciatic nerve axotomy in rats. The invention therefore further relates to the use of IL6IL6 chimera for manufacture of a medicament to induce, enhance or accelerate remyelination, in particular after nerve damage or trauma or axonal injury.

The addition of IL6IL6R recombinant protein to organotypic cultures was further found to induce a prolonged protective effect from neurotoxic agents. The invention therefore also relates to the use of IL6RIL6 chimera for manufacture of a medicament to induce, enhance, prolong or accelerate neuroprotection, in particular from neurotoxic agents, and to inhibit, reduce or decelerate neuronal death, which may be due to apoptosis, for example.

The present invention concerns the use of the "IL6RIL6 chimera" (also called "IL6RIL6" or IL-6 chimera), which is a recombinant glycoprotein obtained fusing the entire coding sequence of the naturally-occurring soluble IL-6 Receptor 6-Val to the entire coding sequence of mature naturally-occurring IL-6, both from human origin. The IL6RIL6 chimera may be produced in any adequate eukaryotic cells, such as yeast cells, insect cells, and the like. It is preferably produced in mammalian cells, most preferably in genetically engineered CHO cells as described in WO 99/02552. Whilst the protein from human origin is preferred, it will be appreciated by the person skilled in the art that a similar fusion protein of any other origin may be used according to the invention, as long as it retains the biological activity described herein.

More particularly, the present invention concerns the use of IL6RIL6 chimera to stimulate the differentiation of progenitor or differentiated glial cells into myelinating cells.

As demonstrated herein the IL6RIL6-induced myelinating cells differentiation process involves both, activation of genes required for the formation of the myelin sheath around neuronal axons, as well as repression of a gene required for the maintenance of non myelinating phenotypes. In accordance with the present invention it has been observed that the addition of IL6RIL6 chimera to cultures of embryonic dorsal root ganglia (eDRG) cells, isolated from mice embryos at days 14–15 of gestation, has a profound effect on the development of the Schwann cell precursors present in the DRG. After 2–5 days in culture, there is a marked increase in the number of the embryonic Schwann cells, a marked phenotypic change in these cells, which start to wrap their membrane around the DRG axons, and an induction of MBP. In accordance with the present invention it has been further observed that in a co-culture of Schwann cells with neurons the IL-6 chimera can induce a significant increase in the binding of Schwann cells along the non-myelinated axons within 5 hours. The Schwann cells, which were labeled with fluorogold, elongate and after a few days their fluorescent cytoplasm could be seen to form a regular sheath around the axons. Without the chimera, or with NGF, the Schwann cells bind much less and do not form a sheath.

Therefore, the invention further relates to the use of IL6RIL6 chimera for the manufacture of a medicament to induce Schwann cell proliferation and/or differentiation, as well as to the myelination by Schwann cells in the peripheral neural system. In accordance with the present invention it has further been shown that the IL-6 chimera can induce remyelination of peripheral nerves in vivo. Following sciatic nerve axotomy in rats and juxtaposition of proximal and distal stumps the IL-6 chimera could induce the regeneration of the peripheral nerves and the remyelination of the transected fibers in vivo. In the presence of the IL-6 chimera a 4 fold increase in the number and thickness of myelinated fibers was found and an increase in the remyelination of the more distant fibers. Therefore, the invention further relates to the use of IL6RIL6 chimera for the manufacture of a medicament to induce remyelination in the peripheral nervous system.

Furthermore it has also been found according to the present invention that the IL-6 chimera can induce the expression of the genes encoding myelin protein components such as MBP, PLP and P0 genes in myelinating cells of the peripheral nervous system such as Schwann cells, and in cells of the central nervous system such as oligodendrocytes. Therefore, the invention further relates to the use of IL6RIL6 chimera for the manufacture of a medicament to induce myelination and/or remyelination by oligodendrocytes in the central nervous system.

It has also been found according to the present invention that the addition of IL6RIL6 chimera to cultures of the B16/F10.9 murine melanoma cell line, induces the expression of the MBP gene within 6–12 hours. Other genes, which encode proteins of the myelin, such as the CNPase gene, are induced whereas expression of genes which are involved in melanogenesis (formation of melanin pigments) such as tyrosinase, are strongly repressed. The F10.9 cells treated by IL6RIL6 also undergo a marked morphological change, and acquire a Schwann-like phenotype. The phenotypic changes and the induction of specific myelin genes support the hypothesis that IL6RIL6 causes a transdifferentiation of the cells from a melanocytic to myelinating state. Since in the embryo, cells migrating from the neural crest can give rise to either melanocytes or myelinating Schwann cells and oligodendrocytes, it is suggested that IL6RIL6 can influence the fate of the cells and promote the formation of myelinating cells. Therefore, the invention also relates to the use of IL6RIL6 chimera for the manufacture of a medicament to induce, promote, enhance or accelerate the formation of myelinating cells in the peripheral and in the central nervous system and/or to induce transdifferentiation of melanocytic cells into myelinating cells.

Moreover, it is shown in accordance with the present invention that IL6RIL6 acts by down-regulating the homeobox gene Pax-3, a gene expressed in embryonic neural crest cells before they differentiate into myelinating Schwann cells (Kioussi and Gruss, 1996). Pax-3 is known to repress MBP gene. Therefore, Pax-3 repression appears to be a key event in the final maturation of the myelinating cells. Hence IL6RIL6 acts on a key differentiation switch (i.e. pax-3 repression).

Pax-3 is a transactivator of the micropthalmia associated transcription factor MITF, which in turn induces and maintains the expression of the tyrosinase and other genes responsible for the melanocytic phenotype. The discovery of the rapid repression of Pax-3 by IL6RIL6 can therefore explain the molecular events which promote the myelinating activity of the neural crest derived cells. After nerve injury, myelinated axons undergo demyelination as part of the Wallerian degeneration. During that process, Schwann cells turn down the expression of MBP gene and other related myelin protein genes. Concomitantly there is an upregulation of Pax-3 and GFAP that denotes a reversion from myelinating SC to non-myelinating and proliferating SC (Kioussi and Gruss, 1996). In accordance with the present invention, the IL6RIL6 chimera appears to be a potent cytokine to revert the process of Wallerian nerve degeneration by repressing Pax-3 and inducing the SC to resume their myelinating activities. The same considerations would apply to brain demyelinating diseases since, like in traumas, the neurodegeneration in these diseases is spurred by a demyelination process driven by macrophages and other inflammatory cells. The invention therefore also relates to the use of IL6RIL6 chimera for the manufacture of a medicament for treatment of nerve damage and/or traumatic nerve degeneration and/or axonal injury.

IL6RIL6 can be injected to mice in which an autoimmune demyelination has been induced by immunization with MBP as a model system for chronic relapsing multiple sclerosis (Cannella et al, 1998). The capacity of IL6RIL6 to induce myelin protein genes and differentiation of myelinating glial cells can be observed in vivo, using this pharmaceutical paradigm. The invention therefore further relates to the use of IL6RIL6 chimera for the manufacture of a medicament for treatment and/or prevention of autoimmune demyelinating diseases, in particular to the treatment and/or prevention of Multiple Sclerosis.

The IL-6 chimera has been also shown to have neuroprotective effects, preventing loss of neuronal cell viability induced by exitotoxic agents in regions involved in memory encoding and exhibiting early degeneration in Alzheimer's disease and ischemia. The IL-6 chimera was found to protect neurons from glutamate induced neurotoxicity. Therefore, the invention relates to the manufacture of a medicament for the protection of neural cells against cell death, in particular due to the effects of neurotoxic agents, and to the treatment and/or prevention of neurodegenerative diseases like Alzheimer's disease, Parkinson's disease or ALS, for example.

Further neurological diseases that may be treated with the IL6RIL6 chimera are strokes, movement disorders, epilepsy, pain and the like.

The definition of "pharmaceutically acceptable" is meant to encompass any carrier, which does not interfere with effectiveness of the biological activity of the active ingredient and that is not toxic to the host to which it is administered. For example, for parenteral administration, IL6RIL6 chimera may be formulated in a unit dosage form for injection in vehicles such as saline, dextrose solution, serum albumin and Ringer's solution.

The IL6RIL6 chimera can be administered to a patient in need of administration thereof in a variety of ways. The routes of administration include intradermal, transdermal (e.g. in slow release formulations), intramuscular, intraperitoneal, intravenous, oral, epidural, topical, and intranasal routes. Any other therapeutically efficacious route of administration can be used, for example absorption through epithelial or endothelial tissues or by gene therapy wherein a DNA molecule encoding the IL6RIL6 chimera is administered to the patient (e.g. via a vector) which causes the IL6RIL6 chimera to be expressed and secreted in vivo. In addition the IL6RIL6 chimera can be administered together with other components of biologically active agents such as pharmaceutically acceptable surfactants, excipients, carriers, diluents and vehicles.

For parenteral (e.g. intravenous, subcutaneous, intramuscular) administration, IL6RIL6 chimera can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

An "effective amount" refers to an amount of the active ingredients that is sufficient to affect the course and the severity of the diseases described above, leading to the reduction or remission of such pathology. The effective amount will depend on the route of administration and the condition of the patient.

The dosage administered, as single or multiple doses, to an individual will vary depending upon a variety of factor, including IL6RIL6 chimera pharmacokinetic properties, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled, as well as in vitro and in vivo methods of determining the remyelination of the nerves.

While the invention will be described in conjunction with specific embodiment thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journals articles or abstracts, published or unpublished patent applications, issue or foreign patents, or any other references, are entirely incorporated by references herein, including all data, tables, figures, and text presented in the cited references. Additionally, the entire contents of the references cited within the references cited herein are also entirely incorporated by references.

The present invention will now be described in more detail in the following non-limiting Examples and the accompanying drawings

EXAMPLES

Example 1

Effect of IL6RIL6 on Myelination and Remyelination in Vitro

In the spinal cord, the dorsal root comprises essentially sensory neurons, which form synapses in the dorsal root ganglia (DRG). During mouse embryogenesis (at day e14–e15), DRGs are a convenient source of neurons and of embryonic Schwann cells which have not yet differentiated into myelinating SC. Procedures to obtain explants of DRGs for in vitro cultures are described by Li (1998). The cultures were performed on glass coverslips placed in the wells of Costar plates, in medium F12/DMEM (Gibco). The coverslips were coated either with collagen or with poly-D-lysine, with essentially similar results. Cultures were either done in medium without growth factor or cytokine additions or in medium supplemented with nerve growth factor (NGF, 40 ng/ml), or in medium supplemented with IL6RIL6 chimeric recombinant proteins (3 µg/ml). The cultures were examined daily by light microscopy with an Olympus inverted microscope linked to a video-camera imaging system (Leica LIDA system). Part of the coverslips were fixed in paraformaldehyde and MBP proteins were labeled with monoclonal primary antibodies to myelin basic proteins and fluorescein-conjugated secondary antibody. Neuronal cell bodies and axons were stained with antibodies to neurofilament protein. Some of the coverslips were examined by scanning electron microscopy (EM).

After 2 to 5 days, the DRG explants cultured without addition showed that the cells growing out of the explant were either polygonal or oval-shaped. However, when NGF was added, the oval shaped cells developed long axonal projections, which formed a thin network stained by antibodies to neurofilaments. Some of the axons were long and bifurcated, but no Schwann cells were observed along the axons. In contrast, cultures with IL6RIL6 showed not only neuronal cells with axons stained for neurofilament, but also Schwann cells appearing as flat cells that had long bipolar extensions with end ramifications. These extensions were not stained for neurofilament proteins. By scanning EM, these Schwann cells were clearly observed along the axonal projections with membrane rufflings starting to wrap around the axon.

Staining with anti-MBP showed positively stained Schwann cells in the IL6RIL6-treated cultures, in particular in arrays of cells which were aligned one after the other. On the other hand, little MBP-specific fluorescence was seen in the NGF-treated cultures without IL6RIL6.

Similar results were observed in DRG cultures from e15 rat embryos.

Schwann cells derived from mouse sciatic nerve were also cultured in vitro with IL6RIL6 1.4 µg/ml and the level of MBP RNA transcript was measured. In comparison, the same cultures were treated with forskolin 20 µM, a chemical which artificially increases the cyclic AMP levels in the cells and is known to induce MBP (Lemke and Chao, 1988). The results showed that IL6RIL6 was as efficient as forskolin to induce MBP gene expression and more efficient to maintain MBP RNA levels after 3 days of culture (FIG. 1).

In a study in 18-day embryo dorsal root ganglion (DRG) cells the IL-6 chimera was found to induce MBP and P0 mRNA expression within 3 days, whereas Pax-3 mRNA was strongly inhibited in the same cell system. A dose-dependent curve of the IL-6 chimera effect on the P0 and MBP gene expression shows maximal effect of the IL-6 chimera at 500 ng/ml. The IL-6 chimera appears, therefore, as an important inducer of myelin gene expression in normal neuroglial cells.

Schwann cell-lines derived from rat sciatic nerve or from rat Dorsal root Ganglion (DRG) cells were generated for further studying the effects of the IL-6 chimera.

The Schwann cell-line derived from rat sciatic nerve was found to respond to the IL-6 chimera, as determined by RT-PCR and Northern blot analysis, by a 2–3 fold P0 gene induction, whose protein product forms about 50% of peripheral nerve myelin.

In order to study the transcriptional activation of the myelin gene components by the IL-6 chimera the MBP promotor was introduced into an expression vector upstream to the luciferase reporter gene and tested in the rat sciatic nerve Schwann cell line. Up to 7-fold induction of the transcriptional-activity from the MBP promotor was observed in response to the IL-6 chimera in these cells in the absence of forskolin. In an additional reporter gene assay the IL-6 chimera was found to induce a 2.5 fold induction in the transcription from the promotor of the P0 gene in these cells.

The above results suggest that the IL-6 chimera has a direct effect on myelin gene transcription in committed Schwann cells.

An additional Schwann cell-line was isolated from the rat Dorsal Root Ganglion (DRG) and named the CH-cell line. This cell line was found to have a slow growth rate and to be dependent for growth on the IL-6 chimera (140 ng/ml). Interestingly, the CH-cells had a stellar morphology resembling that of oligodendrocytes. The cells appeared to be functional with respect to induction of myelination by the IL-6 chimera. The cells expressed P0 and MBP and died when grown in serum containing medium in the absence of the chimera.

Example 2

Inhibition of Oligodendrocyte Proliferation In Vitro

The effects of the IL-6 chimera were studied on cells of the central nervous system. It is established that oligodendrocyte differentiation is associated with the inhibition of their proliferation, thus promoting sheath formation and myelination by oligodendrocytes.

Therefore, the capacity of the IL6R/IL6 chimera to inhibit oligodendrocyte proliferation was tested in vitro. A murine primary oligodendrocyte (oligodendroglial) cell line immortalized with the t-neu oncogene ("oli-neu" cell line) was used in this experiment. The establishment and properties of the oli-neu cell line as well as the culturing conditions are described in Jung et al. (1995).

The proliferation of undifferentiated oli-neu cells was measured after 1, 2 and 3 days in response to different amounts of IL6R/IL6 chimera (1µg/ml, 500 ng/ml, 250 ng/ml, 125 ng/ml and 0 ng/ml (control). The growth rate was quantified by measuring the cellular metabolic activity with a fluorometric/colorimentric growth indicator, Alamar Blue. This agent contains an oxidation-reduction indicator that shows both fluorescence and changes its color in response to chemical reduction of growth medium resulting from cell growth. The agent and assay used are described in Ahmed et al. (1994) and the U.S. Pat. No. 5,501,959.

Figure 2:
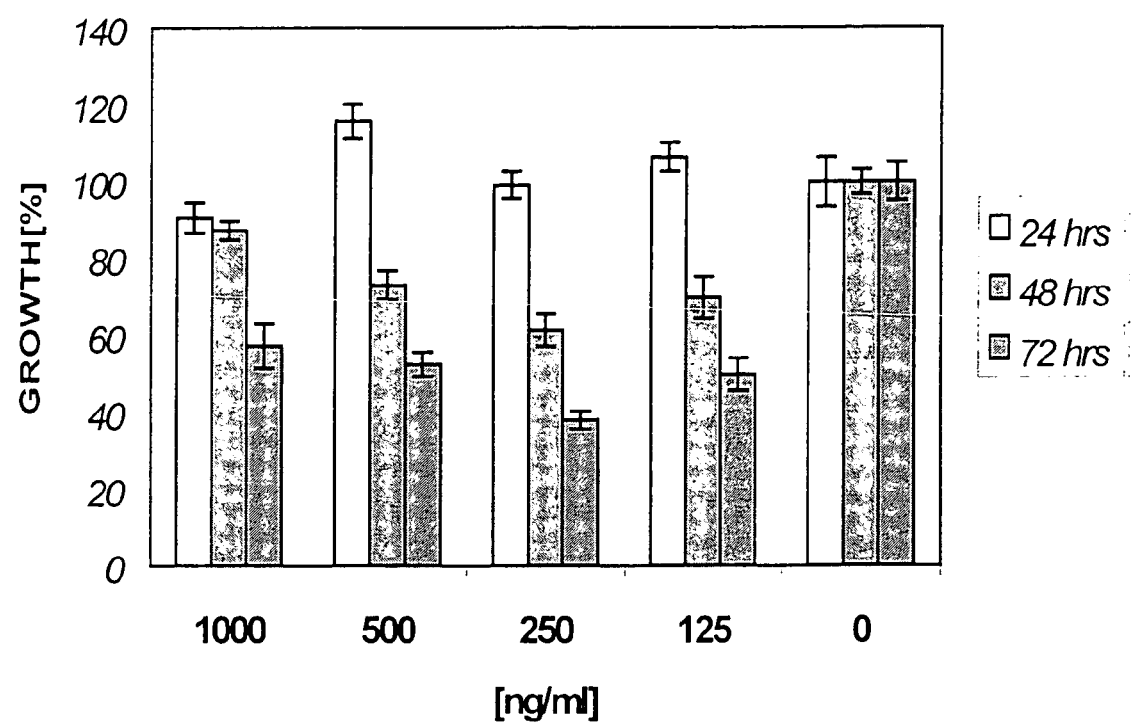
FIG. 2 shows the proliferation of undifferentiated oli-neu cells measured after 24, 48 and 72 hours after treatment with different amounts of IL6R/IL6 chimera.

The results are shown in FIG. 2. Addition of IL6R/IL6 chimera to the culture medium of oligodendrocytes led to a pronounced reduction of growth already after 48 hours. After 72 hours, the growth was reduced to 40 to 50% as compared to the control. Interestingly, the highest amount of IL6R/IL6 chimera (1 µg) was less effective than the lower amounts of 500 to 125 ng/ml.

This experiment shows that the IL6R/IL6 chimera strongly inhibits proliferation of oligodendrocytes in vitro, indicating that it is a promoter of oligodendrocyte differentiation. Since oligodendrocytes are the glia cells producing myelin sheaths in the CNS, the IL6R/IL6 chimera may be an agent actively promoting remyelination in vivo.

Example 3

Impact of IL6R/IL6 Chimera on Oligodendrocyte Morphology

In order to study the effect of IL6 Chimera on the morphology of oligodendroglia, oli-neu cells (see Example 2) were cultured for 3 days in the presence of 1 µg/ml of IL6R/IL6 chimera.

Dibutyl cAMP (dbcAMP) is an agent known to induce differentiation in oligodendrocytes (see, e.g. Jung et al. (1995). In order to investigate, which morphological effect the IL6R/IL6 chimera adds to the effect of dbcAMP, oli-neu cells were pre-treated for 3 days with dbcAMP before addition of IL6R/IL6R/IL6 chimera plus dbcAMP. In parallel, cells were treated with the IL6R/IL6 chimera without pre-treatment.

Changes in morphology were assessed with phase contrast microscopy or by immunohistochemistry staining for oligodendrocyte markers CNPase (2',3'-cyclic-nucleoside-3'-phosphodiesterase) and GalC (sialogangliosides and sulfatides) and using the antibody A2B5, specific for the myelin lipid galactocerebroside.

The addition of IL6R/IL6 chimera clearly induced morphological changes in the oli-neu cells. Cell bodies assembled in rows and their processes became more elongated. The cells themselves were elongated and seemed to be fused, indicating an advanced state of differentiation.

The expression of oligodendrocyte markers was shown by immunohistochemistry. Cells were positive for the oligodendrocyte specific markers A2B5-antigen and CNPase, but were negative for the astroglial marker GFAP, thus showing that indeed, the oligodendrocyte phenotype was maintained.

DbcAMP pretreatment and combined treatment with IL6R/IL6 chimera and dbcAMP increased the number of sheath forming oligodendrocytes after 3 days. Besides elongated cells seen with IL6R/IL6 chimera alone, the morphology of the cells looked even more differentiated. Cells having a sheet-like shape could be observed, indicating an advanced differentiation state.

In conclusion, treatment with the IL6R/IL6 chimera resulted in a morphological change of oligodendrocytes in vitro, thus further supporting its role as an inducer of oligodendroglial differentiation and myelination.

Example 4

IL-6 Chimera Effects on Neuronal Schwann Cell Interaction

By culturing murine DRG in the presence of DNA synthesis inhibitors arabinoseC (AraC) and fluorodeoxyuridine (FudR), neuronal cells can develop axons while glial cell proliferation is inhibited. These DRG cultures can be used as a source of neuronal cells with non-myelinated axons. Schwann cells are exogenously added to these cultures to study the interaction between neurons and Schwann cells.

Rat sciatic nerve Schwann cell lines cells were labeled with fluorogold, a label that penetrates the cell membrane lipid bi-layer and is maintained for an extensive period of time without affecting cell function. Co-culture of the neuronal cells with these Schwann cells in the presence of the IL-6 chimera leads to a significant increase in the binding of the Schwann cells along the axons cells within 5 hours. The cells elongate and after a few days their fluorescent cytoplasm can be seen to form a regular sheath around the axons. Without the chimera, or with NGF, the Schwann cells bind much less and do not form a sheath. These results show that the IL-6 chimera has a very rapid effect on the interaction of glial cells with neurons, suggesting that adhesion molecules are induced or activated. This system allows to study the various steps in the myelination process which are affected by the IL-6 chimera.

Example 5

Effect of IL6R/IL6 Chimera on Myelination in Mixed Cultures of Neurons and Oligodendrocytes In order to further investigate the myelination inducing activity of IL6R/IL6 chimera, dissociated cultures from murine E15 (embryonal day 15) cerebral hemispheres were prepared. The preparation and culture conditions are described by Lubetzki et al. (1993). The primary cells were maintained in culture for 8 days before addition of IL6R/IL6 (1.5 ug/ml) for 11 days.

MBP (myelin basic protein) and the oligodendrocyte specific protein PLP (ProteoLipid Protein) are markers for mature and/or myelinating oligodendrocytes and are major constituents of CNS myelin. They can therefore be used as markers for assessing active myelination taking place in the cell culture.

Under the conditions of the culture, at day 4, there is no myelination. Therefore, day 4 mRNA was used as a calibrator control in this experiment. At day 19, under the culture conditions, myelination in the cell culture is observed.

Thus at days 4 and 19, mRNA was extracted from treated and non-treated wells, in order to quantify MBP and PLP mRNA.

The mRNAs for MBP, PLP and GAPDH, which served as an internal control RNA, were measured by real-time quantitative RT-PCR (Medhurst et al. (2000) using a PE Applied Biosystems Prism model 7700 sequence detection instrument.

The results are summarized in Table I below. Two independent experiments were carried out. The mRNA expression is indicated as fold expression of the control RNA at day 4. In both experiments, the IL6R/IL6 chimera clearly enhanced the expression of MBP and PLP by twofold, again supporting the role of IL6R/IL6 chimera as an inducer or enhancer of myelination.

TABLE I

MBP and PLP expression in primary cortical cultures

|  | Control day 4 | Control day 19 | IL6R/IL6 chimera day 19 |
|---|---|---|---|
| Experiment I |  |  |  |
| MBP | 1 | 72 | 181 |
| PLP | 1 | 1265 | 2157 |
| Experiment II |  |  |  |
| MBP | 1 | 187 | 2157 |
| PLP | 1 | 1884 | 4198 |

In conclusion, examples 1 to 5 show that the IL6R/IL6 chimera has an anti-proliferative, differentiation and myelination inducing activity. This activity of IL6R/IL6 chimera strongly suggests a beneficial effect of IL6R/IL6 chimera in peripheral and central nervous system remyelination. This effect can be exploited in all disorders based on myelination defects, demyelination or insufficient myelination of the CNS or PNS neurons. The IL6R/IL6 chimera may therefore be an effective agent to treat re- and/or demyelination disorders like Multiple Sclerosis, for example.

Example 6

The Effect of the IL-6 Chimera on Peripheral Nerve Regeneration In Vivo

Following sciatic nerve axotomy in rats and juxtaposition of proximal and distal stumps, peripheral nerves can be induced to regenerate and transected fibers can be induced to remyelinate in vivo (Sahenk et al. 1994). The effect of the IL-6 chimera on remyelination of peripheral nerves following axotomy was examined. The rats (7 animals) were given sIL-6/IL-6 chimera intraperitoneally every second day at a dose of 100 mcg/Kg for 12 days beginning on the day of surgery. Control animals (9 rats) were injected with PBS. After 12 days, sections of the regenerating nerve 2.5 and 5 mm below axotomy were analysed by transmission electron microscopy and the number of positive fibers was evaluated.

In the presence of the IL-6 chimera a 2.5-fold increase in the number of myelinated fibers was found at a 2.5-mm distance below axotomy compared to PBS treated controls. The chimera was further found to increase the remyelination of the more distant fibers inducing a 5.2 fold increase in the number of myelinated fibers at 5 mm distal to the section. This is important since remyelination decreases as the distance from the section increases. CNTF effects have been observed at 0.5 mm from the section, but with the IL-6 chimera the effect seems much more extended and greater at 5 mm than at 2.5 mm. Also the thickness of myelinated fibers increased over 2 fold after treatment with the chimera. Overall the IL-6 chimera appears to induce remyelination of about 10% of fibers as compared to intact non-axotomised rats.

Example 7

Induction of MPB Gene by IL6RIL6 in Cultures of Melanoma B16-F10.9 Cells

The embryonic origin of skin melanocytes, which produce the melanin pigments, and of Schwann cells is from common precursor cells migrating out of the neural crest in e8 mouse embryos. Melanomas are malignant tumors developing in the skin from melanocytes, and are therefore also derived from neural crest ancestors. The B16 cell line is derived from a spontaneous melanoma of Balb/c mice, and the F10.9 clone was isolated from B16 for its highly malignant metastatic phenotype. The F10.9 cells, as other B16 cells, produce black eumelanin pigment and are rich in tyrosinase, the first enzyme of the melanogenic pathway (Bertolotto et al, 1996).

F10.9 cells were seeded in 96-well microplates at 30,000 cells/well and cultured for 3 days in DMEM medium with 10% FCS, without or with IL6RIL6 at concentrations of 0.3–1 µg/ml. Total cell RNA was extracted and analysed by Northern blots with cDNA probes for MBP. The MBP mRNAs were induced very strongly at 48 by IL6RIL6 in the F10.9 cells (FIG. 3A). A time course study showed that the increase in MBP RNA started at 12 hours following the addition of the IL6RIL6 chimera to the cell cultures.

The IL6RIL6 chimera induces not only MBP gene expression but also the cyclic 2'3' AMP phosphodiesterase or CNPase, which is another component of the myelin and a marker for differentiated Schwann cells. The cells also developed prolonged extensions at opposite poles of the cell body, and aligned in long arrays as typical of Schwann cells in cultures.

Surprisingly, IL6RIL6 switched the phenotype of the F10.9 cells from melanin producing cells to myelin producing Schwann cells. The tyrosinase enzymatic activity and the production of melanin were completely lost at 48 hours after addition of the IL6RIL6 chimera to the cells.

MITF is a transcription factor that activates the tyrosinase gene (Bertolotto et al, 1996). The treatment of F10.9 cells by IL6RIL6 strongly repressed the MITF gene expression. MITF itself is transactivated by the homeotic transcription factor Pax-3 (Watanabe et al, 1998) and measurements of Pax-3 mRNA in the IL6RIL6 treated F10.9 cells showed that Pax-3 expression decreases starting from 6 hours and up to 48 hours (FIG. 3B). Pax-3 is known to repress the MBP gene (Kioussi and Gruss, 1996). The effect of the IL6RIL6 chimera can, therefore, be ascribed to a gene regulation effect on the Pax-3 homeobox gene, which is expressed during embryonic Schwann cell development prior to myelination, and has to be repressed for myelination to occur. Moreover, in degenerating demyelinating nerves, Pax-3 is re-expressed in the Schwann cells of when these cells stop to produce MBP. It is, therefore, of great importance that IL6RIL6 can both repress Pax-3 and cause the differentiation of Schwann cells into myelinating cells by inducing myelin protein genes.

Example 8

Injections of IL6RIL6 in a Murine Model of Chronic Relapsing Multiple Sclerosis

Mice of the SJL/J strain develop experimental autoimmune encephalomyelitis (EAE) following immunisation with 0.4 mg bovine MBP in incomplete Freund's adjuvant containing 60 µg *Mycobacterium tuberculosis* H37Ra (Difco). The disease can be passively transferred to syngeneic recipient by intravenous injection of 30 million lymph node cells taken 10 days after immunisation. The clinical signs of paralysis appear after a week to 10 days. An acute phase of disease is followed later by remissions and relapses. IL6RIL6 is injected to these mice intraperitoneally or subcutaneously at doses of 1, 3 and 5 µg per mice (body weight about 25 g). The injections are given 4 times per week for at least 3 weeks, starting at either day 3 or day 7 after the passive transfer. The clinical score of the animals is followed and graded as: 1) loss of tail rigidity; 2) hindlimb weakness; 3) limb paralysis on one side; 4) limb paralysis on both sides; 5) lethality. The brain and spinal cord of animals is examined by light microscopy following staining of myelin by luxol fast blue. The effect of IL6RIL6 on reduction in clinical grade and reduction of demyelination of white brain matter can be ascertained.

Example 9

Neuroprotective Effect of the IL6 Chimera on Neuronal and Oligodendroglial Neurocytotoxicity Organotypic cultures provide a unique strategy with which to examine many aspects of brain physiology and pathology. Long-term slice cultures from the hippocampus, a region involved in memory encoding and one that exhibits early degeneration in Alzheimer's disease and ischemia, are particularly valuable in this regard due to their expression of synaptic plasticity mechanisms (e.g., long-term potentiation) and responsiveness to pathological insults (e.g., excitotoxicity).

The cultures were prepared as previously described by Bahr et al. (Bahr 1995) with minor modifications. Hippocampi were dissected out from eight day old Wistar rats and 400 μm thick slices were laid down on a porous and transparent Millicell-CM membrane (Millipore) and cultured in 6 wells multiwell plates. Four slices were placed on each membrane. Culture medium consisted of 50% minimal essential medium (+25 mM HEPES, +4 mM NaHCO3+ NaOH pH 7.2), 25% horse serum and 25% Hanks' solution, glucose (6.4 g/l), penicillin/streptomycin (10 ml/l), L-glutamine (2 mM). Cultures were kept in a 5% $CO_2$ incubator set at a temperature of 37° C. for at least 3 weeks before being used. Medium was changed every week.

Hippocampal slices were exposed to IL6 or to the IL6 chimera at concentrations ranging from 10 μg/ml to 10 μg/ml for 15 min, thereafter NMDA 50 μM was added for additional 30 min. The cultures were placed in fresh medium with or without IL6 or the IL6 chimera. At least four slices were used for each experimental point. NMDA-induced cell death was evaluated either 1 or 3–7 days after the experimental injury by incubating cultures for 1 hour in fresh medium containing propidium iodide (PI 5 μl/ml). Owing to its hydrophilic property, PI enters into disrupted cells and links to nuclear chromatin. The emitted red fluorescence (marker of cell death) was examined using an inverted fluorescence microscope (Zeiss) associated with an intensified charged-coupled device camera. Quantification of total fluorescence was performed by an image analysis system (Image Pro Plus).

Figure 3:
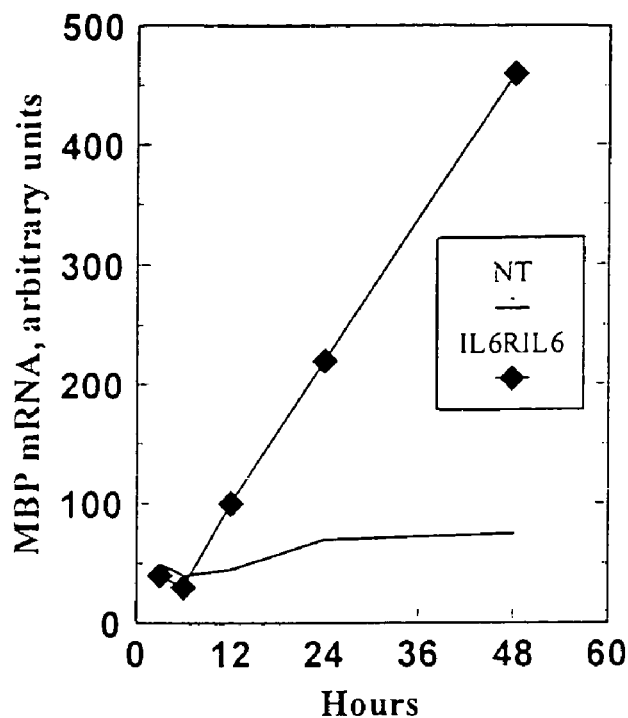
FIG. 3 shows that IL6RIL6 strongly induces MBP mRNAs (A) and decreases Pax-3 mRNA (B) over time in the F10.9 cells. NT designate non treated cells.
Figure 3:
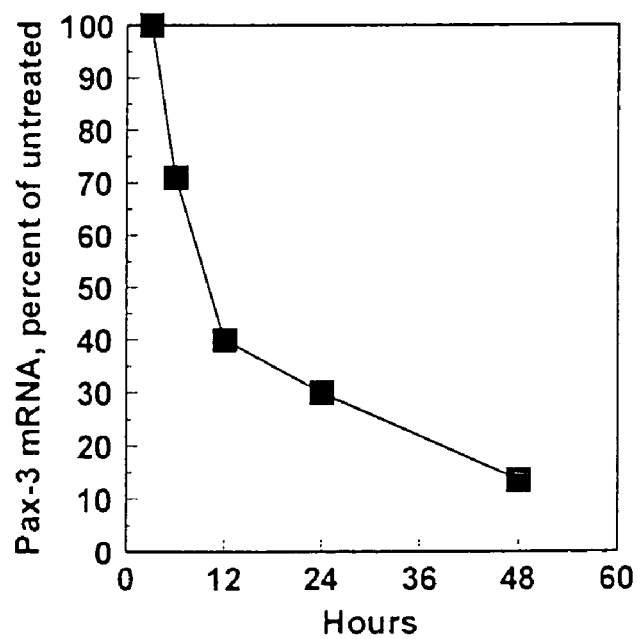

Both IL-6 and the IL-6 chimera were found to protect from NMDA-induced hippocampal cell death. After one day in culture IL-6 at concentration ranging from 0.1 to 10 ng/ml, was found to protect approximately 50%–30% of the neuronal cells respectively, while the IL-6 chimera at concentration ranging from 0.05 to 1 pg/ml protected approximately 40%–75% of the neuronal cells. The maximal protective effect of the IL-6 chimera (protection of 75% of the cells) was observed at a concentration of 0.5 pg/ml (FIG. 3).

Figure 4:
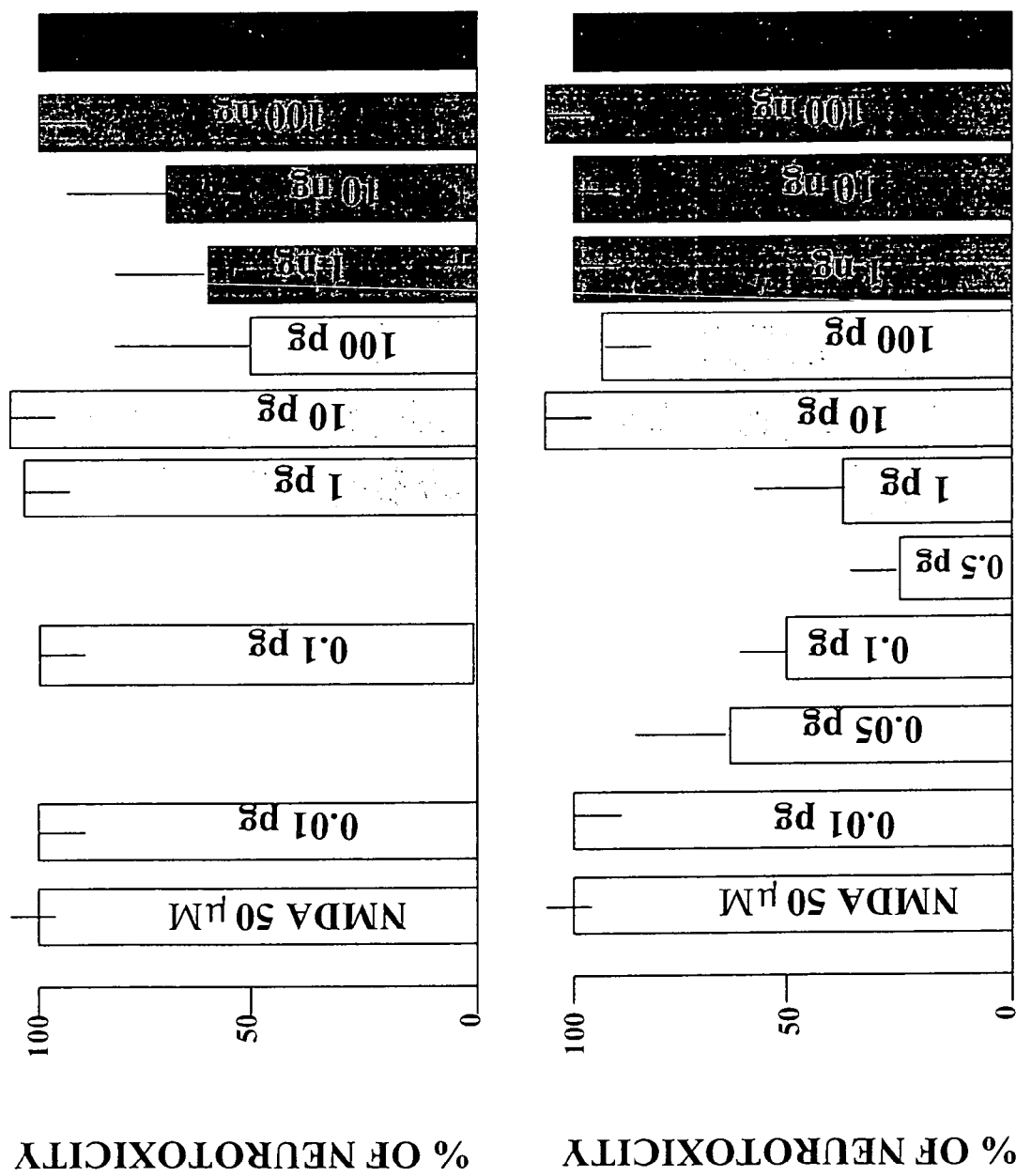
FIG. 4 shows a comparison of neuroprotection by IL-6 alone and the IL-6 chimera on NMDA mediated neurotixicity in hippocampal organotypic slices.
Figure 5:
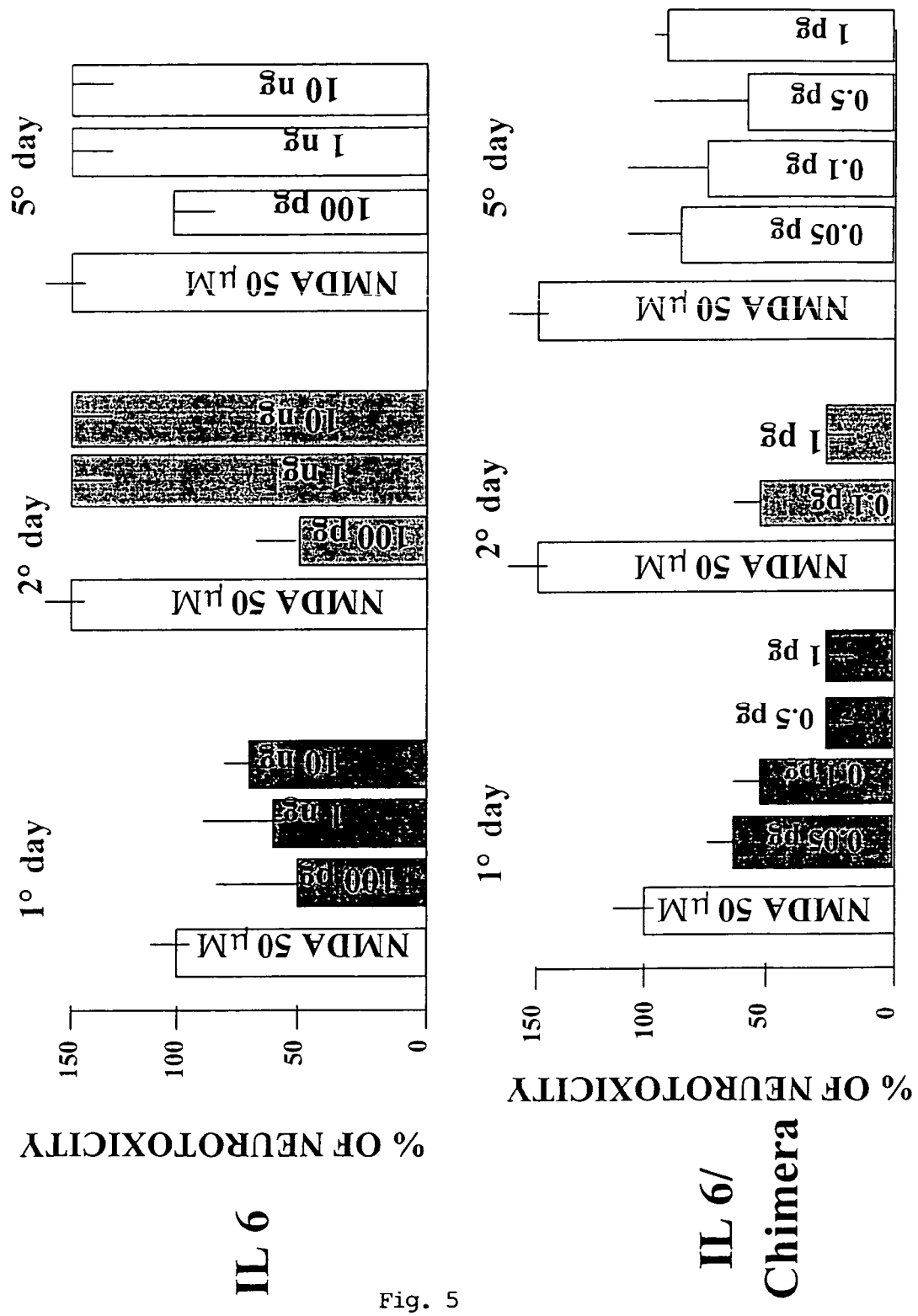
FIG. 5 shows the prolonged neuroprotective effect of the IL-6 chimera vs. the effect of IL-6 alone in hippocampal organotypic slices.

The protective effects of IL-6 were found to decrease with time. Neuronal cell viability declined after treatment and after two days protective effect of IL-6 was maintained only with the 0.1 ng/ml concentration of IL-6 with a protective effect on only 30% of the cells at day 5. In contrast thereto, the IL-6 chimera at a concentration of 0.5 pg/ml had a prolonged protective effect, maintaining approximately 60% of the cells for 5 days (FIG. 4).

The presence of oligodendrocytes in the organotypic slices was determined by immunohistological staining with Gal-C, a specific oligodendrocyte marker. After 2–3 weeks in vitro organotypic slices were exposed for 30 min. to 50 μM NMDA, which induces necrotic cell death of the cells present in these cultures. In fact, as determined by RT/PCR, after treatment with NMDA all MBP expression that is distinctive to oligodendrocytes is lost in these cultures.

Activation of glutamate ionotropic receptors represents the primary event in the neurotoxicity process triggered by excitatory amino acids. Primary cultures of new born rat cerebella neurons (which contain >97% neurons) were employed for studying the effects of the IL6 chimera on glutamate-induced neurotoxicity and compared to the effects of IL-6.

Primary cultures of cerebellar granule cells were prepared from 8 day-old Sprague-Dawley rat pups as previously described (Pizzi et al. 1993). Cells were plated onto poly-L-Lysine-coated dishes and cultured in basal Eagle's medium containing 10% heat-inactivated foetal bovine serum, glutamine (2 mM), gentamicin (50 μg/ml), and KCl (25 mM), at a density of $2.5 \times 10^5$ cells/cm². Cytosine Arabinoside (10 μM) was added to the cultures 18 h after seeding to prevent non neuronal cell proliferation. Experiments were carried out after culturing the neurons for 10 days.

Unless otherwise indicated, cultures were exposed for 15 min to 50 μM glutamate in a $Mg^{2+}$-free Locke's solution. IL6 or the IL6 chimera were added 5 min before glutamate treatment. Dishes were then returned to cultured conditioned medium at 37° C. in 95% air/5% $CO_2$ and cell viability was measured 18–24 hours later.

Cell viability was evaluated 18 h later by intravital staining with fluorescein diaceate and propidium iodide mixture, as previously described (Pizzi et al. 1993). The percentage of surviving neurons in the monolayer was computed by assessing the ratio between the fluorescein diacetate (green viable cells) and fluorescein diacetate plus propidium iodide staining (total cells) in photomicrographs of three representative fields from each monolayer. Values were taken from three sister dishes.

While no protective effect on rat cerebellar granule cells was induced with IL-6 at doses ranging from 0.1 to 10 ng/ml, 0.1 pg/ml and 1 pg/ml of the IL-6 chimera protected respectively 40–20% of the neuronal cells from glutamate-induced neurotoxicity.

Example 10

Effect of IL6R/IL6 Chimera on Survival of Superior Cervical Ganglia Neurons after NGF Withdrawal The neuroprotective effect exerted by the IL6R/IL6 chimera was also studied in a peripheral neuronal culturing system.

Superior cervical ganglia (SCG) neurons were isolated from P0-P3 (postnatal days 0 to 3) rat superior cervical ganglia. The neurons were kept for 4 days in a medium containing 5% rat serum and NGF. NGF is needed by the neuron for survival, whereas NGF deprival leads to dying of the cells due to induction of apoptosis. The initial medium was replaced by NGF-free medium containing neutralizing antibodies to the growth factor. At this point of time, 0.1 or 1 pg/ml IL6R/IL6 chimera were added in 1% DMSO final concentration. The culture was kept at 37° C. for 24 hours.

The effect of IL6R/IL6 chimera on the survival of NGF-deprived neurons after 24 hours of treatment was assessed by microscopy as well as by the mitochondrial activity of the cells as measured by the MTT assay, which is described in detail by Mosmann (1983). The concentrations of IL6R/IL6 chimera used did not show any toxic or morphological effect on the SCG neurons treated with NGF.

Figure 6:
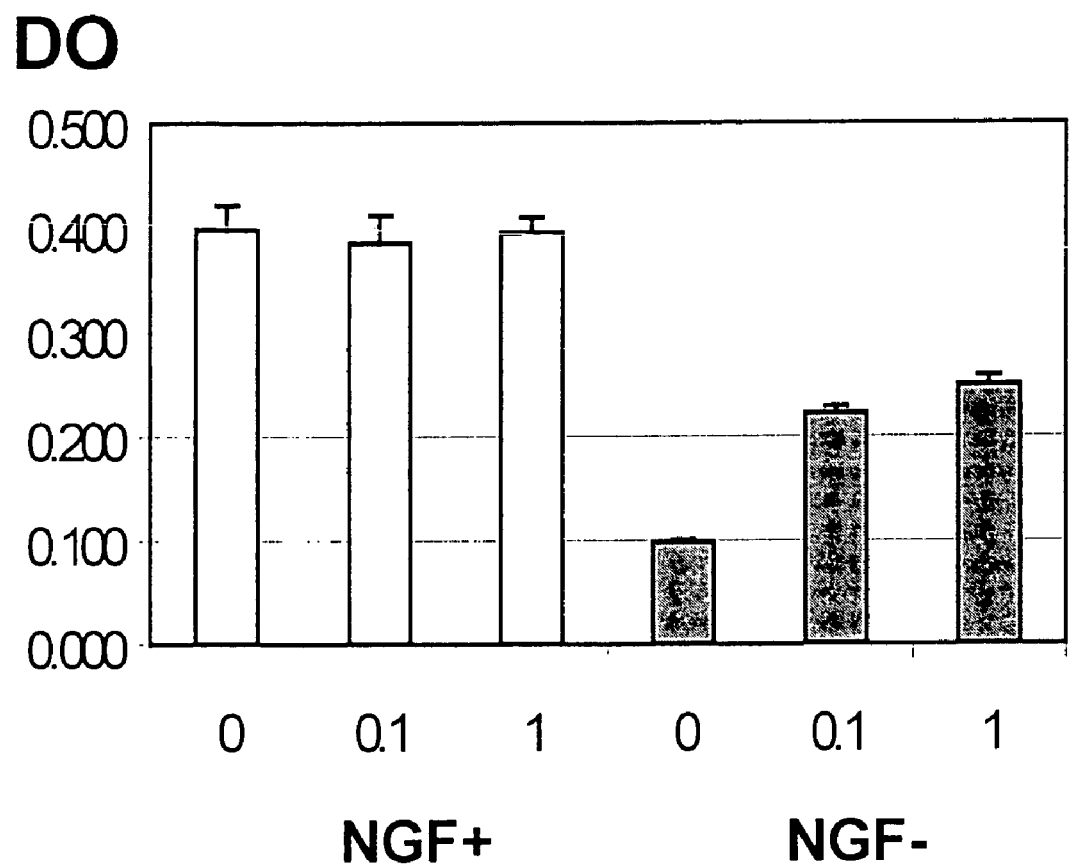
FIG. 6 shows the effect of IL6R/IL6 chimera on the survival of NGF-deprived neurons after 24 hours of treatment as measured by the MTT assay.

Addition of IL6R/IL6 chimera in concentrations of 100 ng/ml and 1 μg/ml rescued up to 40% of SCG neurons from neuronal death, which had been induced by NGF deprivation. as can be seen from the results of the MTT assay (FIG. 6). Thus, IL6R/IL6 chimera has a neuroprotective effect on peripheral neurons, suggesting an activity in neurodegenerative diseases like, e.g. Alzheimer Disease, Parkinson Disease or ALS (Amyotrophic Lateral Sclerosis).

Having now fully described the invention, it will be appreciated by those skilled in the art that the same can be performed within a wide range of equivalent parameters, concentrations and conditions without departing from the spirit and scope of the invention and without undue experimentation.

REFERENCES

Abramsky, O. and Ovadia, H. (1997) Frontiers in Multiple Sclerosis, clinical research and therapy. Martin Dunitz publisher, London.

Ahmed S. A. Gogal, R. M., Jr. Walsh, J. E. (1994) A new rapid and simple non-radioactive assay to monitor and determine the proliferation of lymphocytes: an alternative to [$^3$H]thymidine incorporation. J. of Immunol. Methods 170, 211–224

Anderson, D. J. (1997) Cellular and molecular biology of neural crest cell lineage determination. Trends Genet. 13, 276–280.

Bahr, B. A. (1995). Long-term hippocampal slices: a model system for investigating synaptic mechanisms and pathologic processes. J Neurosci Res, 42, 294–305.

Bertolotto, C., Bille, K., Ortonne, J. P. and Ballotti, R. (1996) Regulation of tyrosinase gene expression by cAMP in B16 melanoma involves two CATGTG motifs surrounding the TATA box: implication of the microphtalmia gene product. J. Cell. Biol. 134, 747–755.

Bonni A, Sun Y, Nadal-Vicens M, Bhatt A, Frank DA, Rozovsky I, Stahl N, Yancopoulos G D, Greenberg ME (1997) Regulation of gliogenesis in the central nervous system by the JAK-STAT signaling pathway. Science 278, 477–483

Cannella, B., Hobam, C. J. Gao, Y. L. et al (1998) The neuregulin, glial growth factor 2, diminishes autoimmune demyelination and enhances remyelination in a chronic relapsing model for Multiple Sclerosis. Proc. Natl. Acad. Sci. USA, 95, 10100–10105.

Chebath, J., Fischer, D., Kumar, A., Oh, J. W., Kollet, O., Lapidot, T., Fischer, M., Rose-John, S., Nagler, A., Slavin, S. and Revel, M. (1997) Interleukin-6 receptor-Interleukin-6 fusion proteins with enhanced Interleukin-6 type pleiotropic activities. Eur. Cytokine Netw. 8,359–365.

Chen, L. E., Liu, K. Seaber, A. V., Katragadda, S., Kirk, C and Urbaniak, J. R. (1998) Recombinant human glial growth factor 2 (rhGGF2) improves functional recovery of crushed peripheral nerve (a double-blind study). Neurochem. Int., 33, 341–351.

Fraser, S. E. and Bronner-Fraser, M. (1991). Migrating neural crest cells in the trunk of the avian embryo are multipotent. Development 112, 913–920.

Gadient, R. A. and Otten, U. H. (1997) Interleukin-6 (IL-6)—A molecule with both beneficial and destructive potentials. Prog. Neurobiol., 52, 379–390.

Hartung, H. P., van der Meche, F. G/, Pollard, J. D. (1998) Guillain-Barre syndrome, CIDP and other chronic immune-mediated neuropathies. Curr. Opin. Neurol., 11, 497–513

Hirota, H., Kiyama, H., Kishimoto, T. and Taga, T. (1996) Accelerated nerve regeneration in mice by upregulated expression of Interleukin (IL) 6 and IL-6 receptor after trauma. J. Exp. Med. 183, 2627–2634.

Ho, P. R., Coan, G. M., Cheng, E. T., Niell, C., Tarn, D. M., Shou, H., Sierra, D. and Terris, D. J. (1998) Repair with collagen tubules linked with brain-derived neurotrophic factor and ciliary neurotrophic factor in a rat sciatic nerve injury model. Arch. Otolaryngol. Head Neck Surg., 124, 761–766.

Ip N Y, Nye S H, Boulton T G, Davis S, Taga T, Li Y, Birren S J, Yasukawa K, Kishimoto T, Anderson D J, et al (1992) CNTF and LIF act on neuronal cells via shared signaling pathways that involve the IL-6 signal transducing receptor component gp130. Cell 69:1121–32

Jessen, K. R. and Mirsky, R. (1991). Schwann cell precursors and their development. Glia 4, 185–194.

Jung, M., Kramer, E., Grzenkowsko, M., Blakemore, W., Aguzzi, A., Khazaiu, K., Chlichlia, K., von Blankenfeld, G., Kettenmann, and Trotter, J. (1995). Lines of Murine Oligodendroglial Precursor Cells Immortalized by an Activated neu Tyrosine Kinase Show Distinct Degrees of Interaction with Axons In Vitro and In Vivo. Eur. J. of Neuroscience 7, 1245–1265

Kahn, M. A. and De Vellis, J. (1994) Regulation of an oligodendrocyte progenitor cell line by the interleukin-6 family of cytokines. Glia. 12, 87–98.

Kollet, O., Aviram, R., Chebath, J., ben-Hur, H., Nagler, A., Shultz, L., Revel, M. and Lapidot, T. (1999) The soluble IL-6 receptor/IL-6 fusion protein enhances maintenance and proliferation of human $CD34^+CD38^{-/low}$/SCID repopulating cells (SRC) in vitro. Blood, in press.

Kioussi, C. and Gruss, P. (1996) Making a Schwann. Trends Genet., 12, 84–86.

Lee, D. A., Zurawel, R. H. and Windebank, A. J. (1995) Ciliary Neurotrophic factor expression in Schwann cells is induced by axonal contact. J. Neurochem. 65, 564–568.

Lemke, G. and Chao, M. (1988). Axons regulate Schwann cell expression of the major myelin and NGF receptor genes. Development 102, 499.

Li, R. (1998) Culture methods for selective growth of normal rat and human Schwann cells. Meth. Cell. Biol., 57, 167–186.

Lipton, S. A., and Rosenberg, P. A. (1994). Excitatory amino acids as a final common pathway for neurologic disorders. N Engl J Med, 330, 613–22.

Lubetzki, C., Demerens, C., Anglade, P., Villarroya, H., Frankfurther, A., Lee., V. M.-Y., and Zalc, B. (1993) Even in culture, oligodendrocytes myelinate solely axons. PNAS 90, 6820–6824.

Mayer, M., Bhakoo, K. and Noble, M. (1994) Ciliary Neurotrophic factor and Leukemia Inhibitory factor promote the generation, maturation and survival of oligodendrocytes in vitro. Development, 120, 143–153.

McDonald, J. W., Althomsons, S. P., Hyrc, K. L., Choi, D. W., and Goldberg, M. P. (1998). Oligodendrocytes from forebrain are highly vulnerable to AMPA/kainate receptor-mediated excitotoxicity. Nat Med, 4, 291–7.

Medhurst, A. D., Harrison, dbcAMP, Read, S. J., Campbell, C. A., Robbins, M. J. and Pangalos, M. N. (2000) The use of TaqMan RT-PCR assays for semiquantitative analysis of gene expression in CNS tissues and disease models. J. Neurosci. Methods 15, 9–20.

Mendel, I., Katz, A., Kozak, N., Ben-Nun, A. and Revel, M. (1998) Interleukin-6 functions in autoimmune encephalomyelitis: a study in gene-targeted mice. Eur. J. Immunol. 28, 1727–1737.

Mosmann, T. (1983). Rapid colorimetric assay for cellular growth and survival: Application to proliferation and cytotoxicity assays. J. Immunol. Methods 65, 55–63

Murakami, M., Hibi, M., Nakagawa, N., Nagakawa, T., Yasukawa, K., Yamanishi, K., Taga, T. and Kishimoto, T. (1993) IL-6 induced homodimerization of gp130 and associated activation of a tyrosine kinase. Science 260, 1808–1810.

Novick, D., Shulman, L. M., Chen, L. and Revel, M. (1992) Enhancement of interleukin-6 cytostatic effect on human breast carcinoma cells by soluble IL-6 receptor from urine and reversion by monoclonal antibodies. Cytokine, 4, 6–11.

Pantoni, L., Garcia, J. H., and Gutierrez, J. A. (1996). Cerebral white matter is highly vulnerable to ischemia. Stroke, 27, 1641–6.

Pizzi, M., Fallacara, C., Arrighi, V., Memo, M., and Spano, P. F. (1993). Attenuation of excitatory amino acid toxicity by metabotropic glutamate receptor agonists and aniracetam in primary cultures of cerebellar granule cells. J Neurochem, 61, 683–9.

Pohlau, D., Aktas, O., Epplen, C. Hartung, H. P., Hoffmann, V. and Przuntek, H. (1998) Promoting remyelination as a future therapeutic principle in Multiple Sclerosis. Nervenarzt, 69, 841–850.

Sahenk, Z., Seharaseyon, J., and Mendell, J. R. (1994). CNTF potentiates peripheral nerve regeneration. Brain Res, 655, 246–50. Stocker, K. M, Sherman, L., Ree, S. and Ciment, G. (1991) Basic FGF and TGF-beta1 influence commitment to melanogenesis in neural crest-derived cells of avian embryos. Development, 111,635–645.

Taga, T., Hibin M., Hirata, Y., Yamasaki, K., Yasukawa, K., Matsuda, T., Hirano, T. and Kishimoto, T. (1989) Interleukin-6 triggers the association of its receptor with a possible signal transducer gp130. Cell, 58, 573–581.

Topliko, P., Murphy, P. and Chamay, P. (1996) Embryonic development of Schwann cells: Multiple roles for Neuregulins along the pathway. Mol. Cell. Neurosc., 8, 71–75.

Toulmond, S., Vige, X., Fage, D., and Benavides, J. (1992). Local infusion of interleukin-6 attenuates the neurotoxic effects of NMDA on rat striatal cholinergic neurons. Neurosci Lett, 144, 49–52.

Trapp, B. D., Hauer, P. and Lemke, G. (1988). Axonal regulation of myelin protein mRNA levels in actively myelinating Schwann cells. J. Neurosci. 8, 3515.

Trojaborg W (1998) Acute and chronic neuropathies: new aspects of Guillain-Barre syndrome and chronic inflammatory demyelinating polyneuropathy, an overview and an update. Electroencephalogr Clin Neurophysiol., 107, 303–316.

Watanabe, A. Takeda, K., Plopis, B. and Tachibana, M. (1998) Epistatic relationship between Waardenburg syndrome genes MITF and Pax3. Nature Genet., 18, 283–286.

Yamada, M., and Hatanaka, H. (1994). Interleukin-6 protects cultured rat hippocampal neurons against glutamate-induced cell death. Brain Res, 643, 173–80.

The invention claimed is:

1. A method for inducing myelination and remyelination of neurons, comprising administering to a patient in need thereof an effective amount of interleukin-6 receptor interleukin-6 (IL6RIL6) chimera, thereby resulting in the induction of myelination or remyelination of neurons.

2. The method of claim 1, for inducing myelination and remyelination of neurons, wherein the patient in need is one suffering from traumatic nerve degeneration or a demyelinating disease of the central nervous system (CNS) or peripheral nervous system (PNS).

3. The method of claim 1, wherein the patient in need is one suffering from multiple sclerosis (MS).

4. A method in accordance with claim 1, wherein said IL6RIL6 chimera is administered together with a pharmaceutically acceptable carrier.

* * * * *